United States Patent
Muckenhirn (10) Patent No.: US 7,623,228 B1
(45) Date of Patent: Nov. 24, 2009

(54) FRONT FACE AND EDGE INSPECTION

(75) Inventor: Sylvain Muckenhirn, Santa Barbara, CA (US)

(73) Assignee: KLA-Tencor Technologies Corporation, Milpitas, CA (US)

(*) Notice: Subject to any disclaimer, the term of this patent is extended or adjusted under 35 U.S.C. 154(b) by 193 days.

(21) Appl. No.: 11/751,559

(22) Filed: May 21, 2007

(51) Int. Cl.
*G01N 21/00* (2006.01)

(52) U.S. Cl. .................................................. 356/237.2

(58) Field of Classification Search ... 356/237.2–237.6, 356/237.1; 702/85
See application file for complete search history.

(56) References Cited

U.S. PATENT DOCUMENTS 5,940,175 A * 8/1999 Sun .......................... 356/237.3
2003/0169916 A1 * 9/2003 Hayashi et al. ............. 382/145
2004/0105093 A1 * 6/2004 Hamamatsu et al. ...... 356/237.4
2004/0207836 A1 * 10/2004 Chhibber et al. ......... 356/237.4
2004/0234360 A1 * 11/2004 Hayashi ..................... 414/217
2005/0094136 A1 * 5/2005 Xu et al. .................. 356/237.3

* cited by examiner

*Primary Examiner*—Tarifur R. Chowdhury
*Assistant Examiner*—Isiaka O Akanbi
(74) *Attorney, Agent, or Firm*—Joshua D. Isenberg; JDI Patent (57) ABSTRACT

A surface and edge inspection system and the method for inspecting a substrate are disclosed. An edge inspection tool performs edge inspection of one or more substrates while a surface inspection tool performs surface inspection of a different substrate. A recipe for the surface inspection may be modified based on the results of the edge inspection.

11 Claims, 11 Drawing Sheets

FRONT FACE AND EDGE INSPECTION

FIELD OF THE INVENTION

This invention generally relates to surface inspection technique and more particularly to process combination of front face inspection and edge inspection.

BACKGROUND OF THE INVENTION

Semiconductor wafers may be inspected for defects such as, e.g., surface imperfections, particles, irregularities in the thickness of thin film coatings, and the like, which may hamper the performance of the semiconductor wafers. Some existing inspection systems direct a beam of radiation on the surface of the semiconductor wafers, then collect and analyze light reflected and/or scattered from the surface to quantify characteristics of the surface.

Traditionally, the wafer edge has been of secondary concern to semiconductor manufactures, since it was considered a non-active area. However, there is a growing industry awareness that wafer edge conditions impact yields, directly and indirectly. For instance, a large scratch, residual slurry or open blister on the bevel can flake or peel off, depositing particles on the front surface that cause the defects. Therefore, additional inspection tools and techniques are desirable to inspect the edge or near edge of semiconductor wafers, compound semiconductor wafers, transparent wafers or thin film disks for defects such as particles, scratches, pits, mounds, cracks, blisters, missing films, chips, and other defects. However, most current inspection tools are macro inspection tools and the inspection techniques include an inspection on the front surface first, manually inspecting the wafer edge with a microscope and comparing density of edge defects to behavior on front surface. The current inspection tools and techniques are time consuming and require a large number of standard samples, which decreases the throughput in semiconductor manufacture.

It is within this context that embodiments of the present invention arise.

BRIEF DESCRIPTION OF THE DRAWINGS

Other objects and advantages of the invention will become apparent upon reading the following detailed description and upon reference to the accompanying drawings in which.

DESCRIPTION OF THE SPECIFIC EMBODIMENTS

Although the following detailed description contains many specific details for the purposes of illustration, anyone of ordinary skill in the art will appreciate that many variations and alterations to the following details are within the scope of the invention. Accordingly, the exemplary embodiments of the invention described below are set forth without any loss of generality to, and without imposing limitations upon, the claimed invention.

Figure 1A:
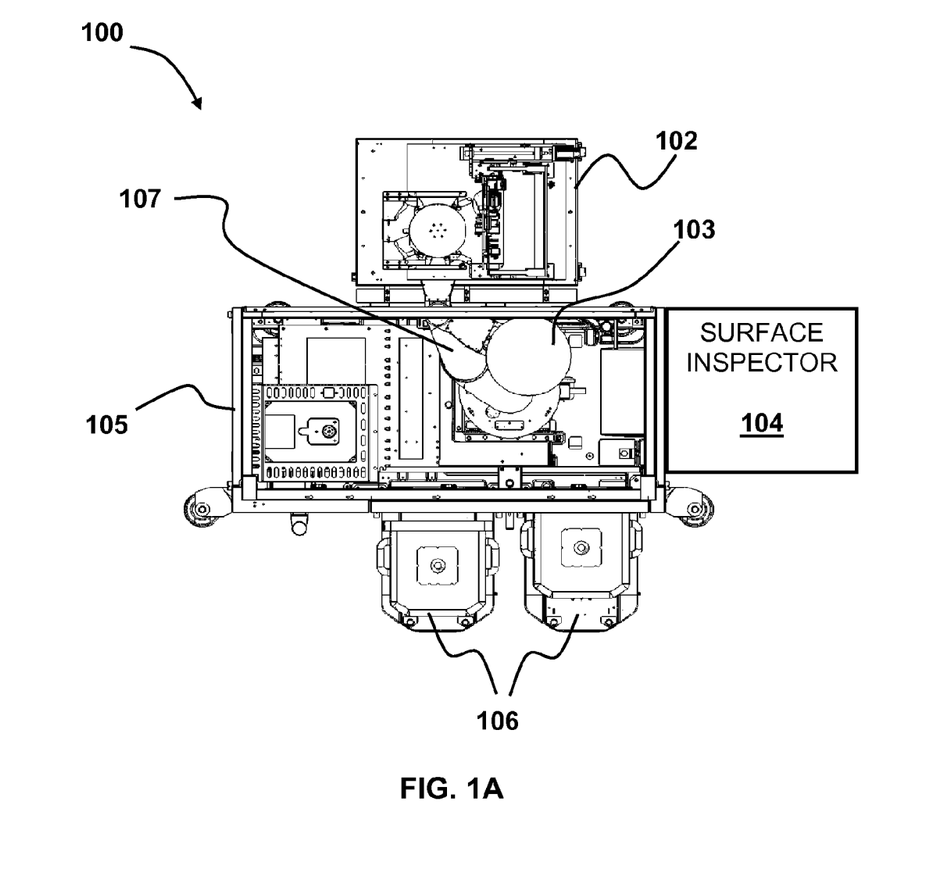
FIGS. 1A-1H are top views of surface and edge inspection systems according to embodiments of the present invention.
Figure 1B:
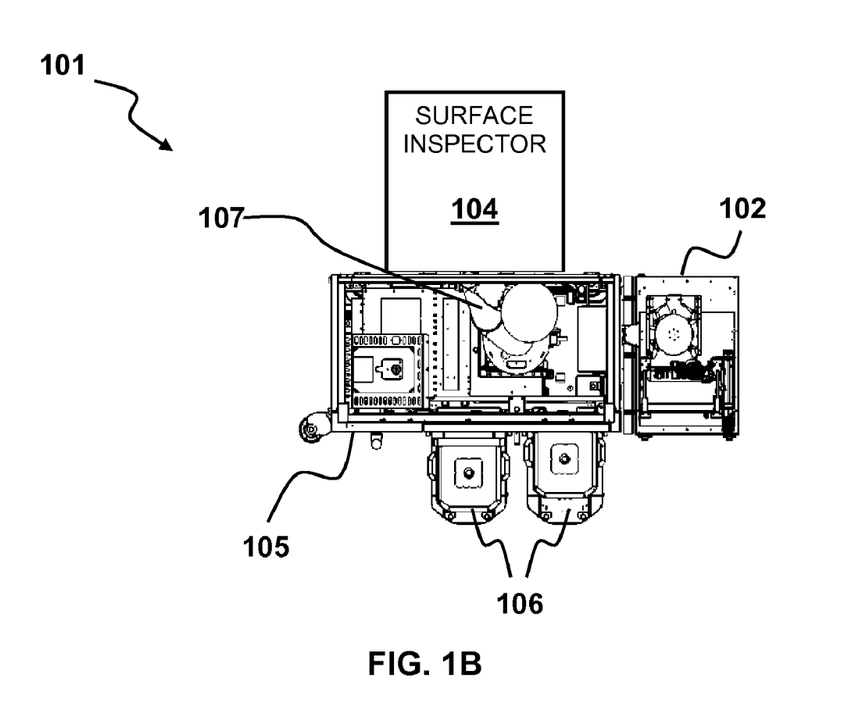

FIGS. 1A-1B are top views illustrating the surface and edge inspection systems according to an embodiment of the present invention. As shown in FIG. 1A, the surface and edge inspection system 100 may include a surface inspection tool 104 and an edge inspection tool 102. By way of example, the surface inspection tool 104 may be situated within an equipment front end module (EFEM) 105 that is adapted to receive one or more substrate pods 106. A transfer mechanism 107, such as a robot arm, may transfer substrates 103, e.g., semiconductor wafers, from the pods 106 to the surface inspection tool 104. By way of example and without loss of generality, the edge inspection tool 102 may be located outside the EFEM 105 behind the surface inspection tool 104. Alternatively, the edge inspection tool 102 may be located outside the EFEM 105 beside the surface inspection tool 102 as shown in the system 101 of FIG. 1B. In either case, the transfer mechanism 107 may transfer the substrates 103 from the surface inspection tool 104 to the edge inspection tool 102 and/or vice versa.

Figure 1C:
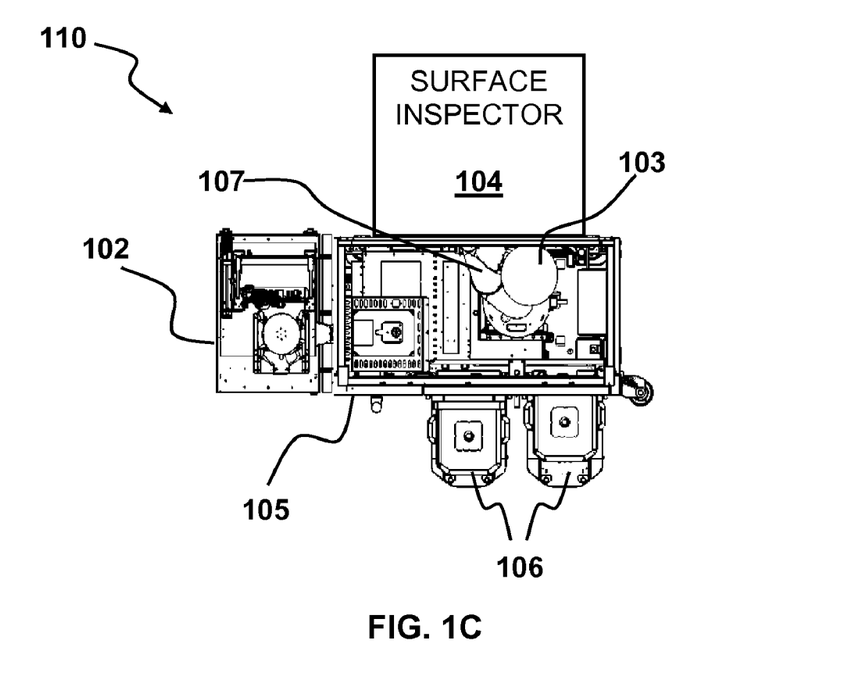
Figure 1D:
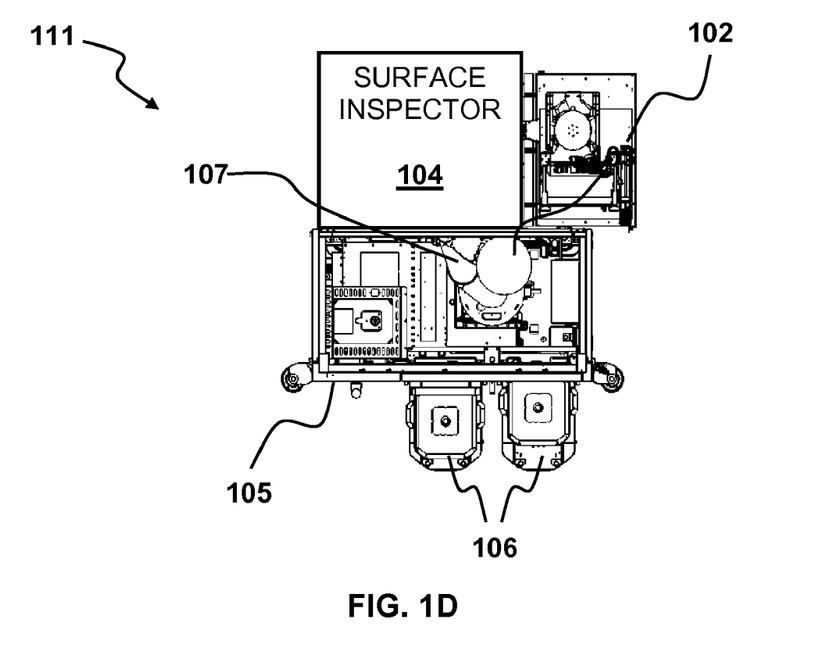
Figure 1E:
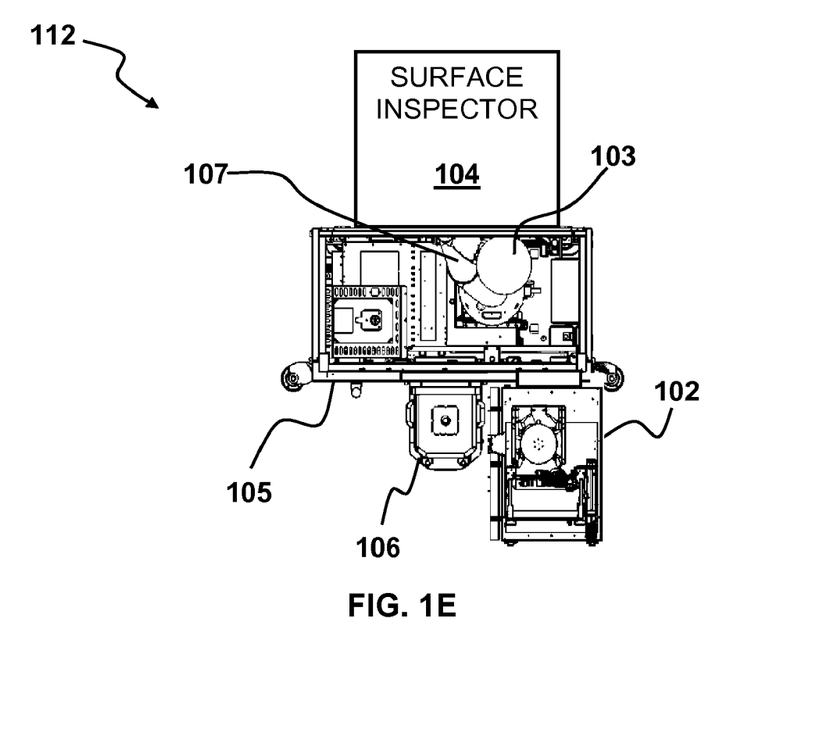

The edge inspection tool 102 may be may located on either side of the EFEM 105 as shown in the surface and edge inspection system 110 of FIG. 1C. Furthermore, the edge and surface inspectors may be integrated to the same side of the EFEM 105, e.g., the front side as in the surface and edge inspection system 111 of FIG. 1D. Furthermore, the edge inspection tool 102 may be integrated into a front side of the EFEM 105, e.g., as a replacement for one of the pods 106 as in the surface and edge inspection system 112 of FIG. 1E.

Figure 1F:
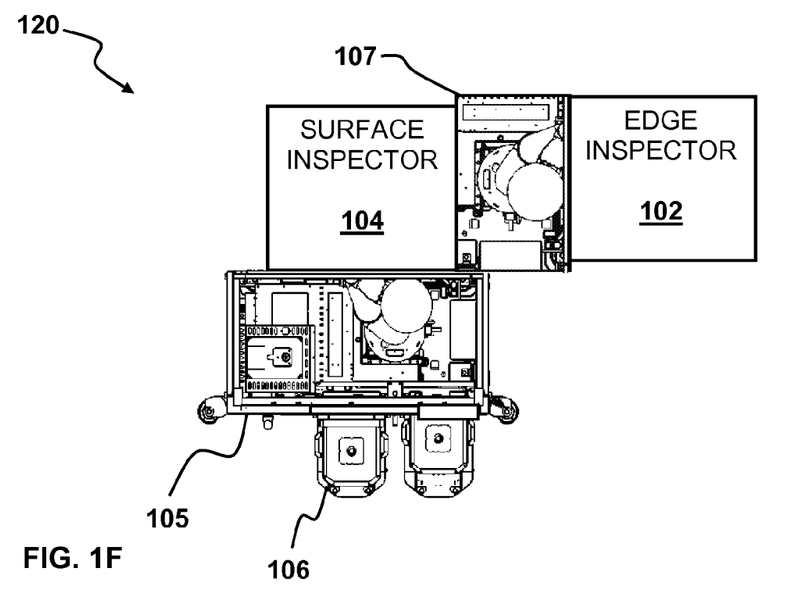
Figure 1G:
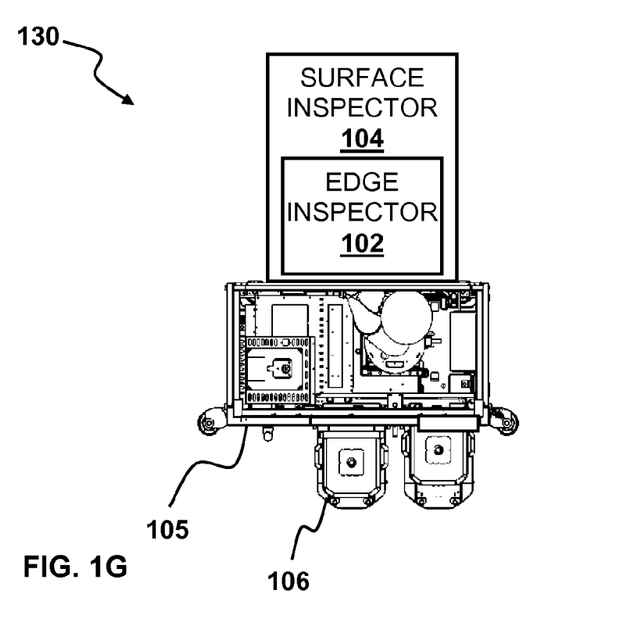

In an alternative embodiment shown in FIG. 1F a surface and edge inspection tool 120 may include an edge inspection tool 102 implemented as an external module on any side of the surface inspection tool 104 with a transfer mechanism 107 between the two tools. Furthermore, as shown in FIG. 1G, a surface and edge inspection system 130 may include an edge inspection tool 102 integrated within the footprint of the surface inspection tool 104. By way of example, such a configuration may be implemented as a dual stage system with one stage dedicated to the surface inspection tool 104 and a second stage dedicated to the edge inspection tool 102.

Figure 1H:
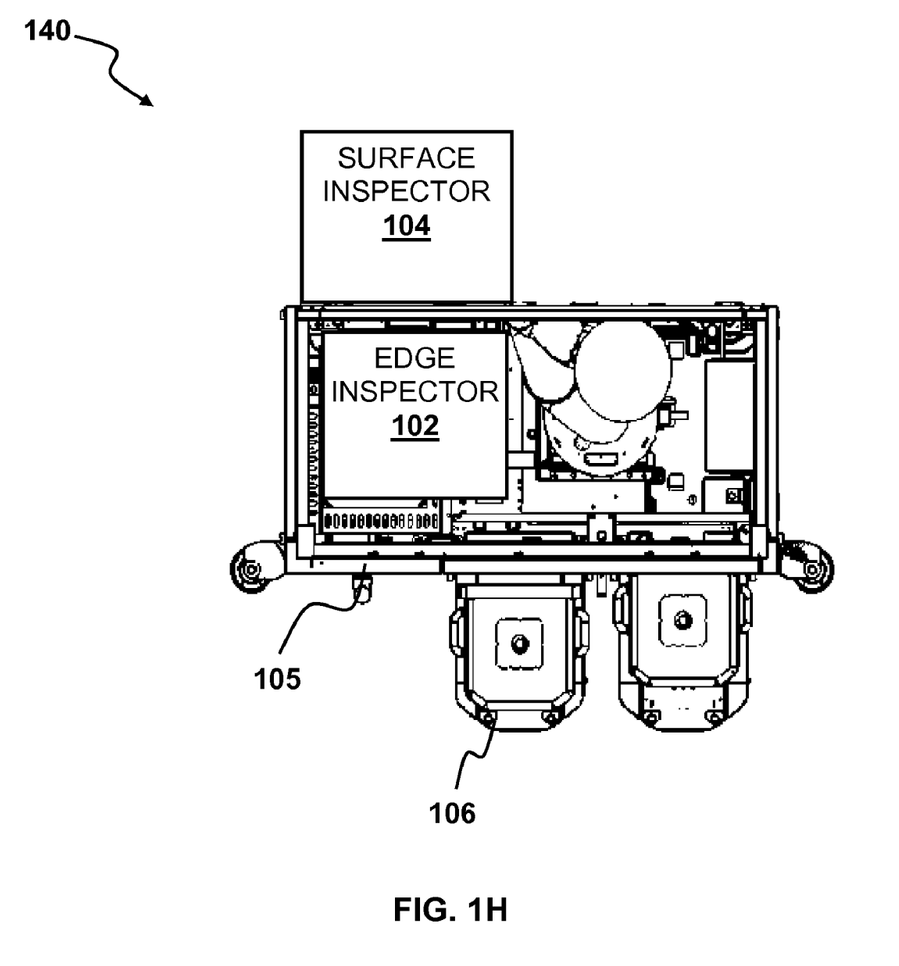

In addition, as shown in FIG. 1H, a surface and edge inspection tool 140 may integrate the edge inspection tool 102 within the footprint of the EFEM 105. The EFEM 105 may include a robot arm 107 with a Z travel capability to allow for vertical stacking of inspection tool modules.

The surface inspection tool 104 and edge inspection tool 102 can use both bright field (BF) and dark field (DF) imaging operations. The surface inspection tool 104 can be, but not limited to, surface inspection systems from KLA Tencor Corporation, such as Candela systems (Candela CS1, Candela CS10, Candela CS2 and Candela CS20), PUMA systems (PUMA 9000 series and PUMA91xx series), Surfscan systems (Surfscan SP2, Surfscan SP2$^{XP}$ and Surfscan SP1 DLS) and Viper systems (Viper 2430, Viper 2435 and Viper 2401).

The edge inspection tool 102 can be, but not limited to, edge inspection systems from KLA Tencor Corporation such as VisEdge CV300.

Figure 2:
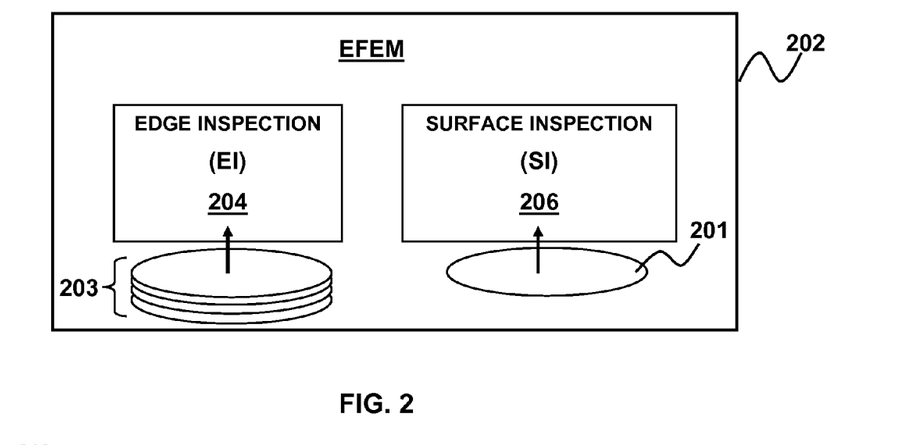
FIG. 2 is a block diagram illustrating a surface and edge system with the surface inspection tool and edge inspection tool integrated inside an equipment front-end module (EFEM) according to an embodiment of the present invention.

In addition, the surface inspection tool and the edge inspection tool can be integrated inside an equipment front-end module (EFEM). As shown in FIG. 2, the edge inspection tool 204 and surface inspection tool 206 are integrated inside an EFEM 202, which reduces additional substrate delivery, load and align time. In embodiments such as those shown in FIGS. 1A-1B and FIG. 2, the edge inspection tool 202 may be configured to perform edge inspection of one or more substrates 203 while the surface inspection tool 206 performs surface inspection of a different substrate 201.

Figure 3A:
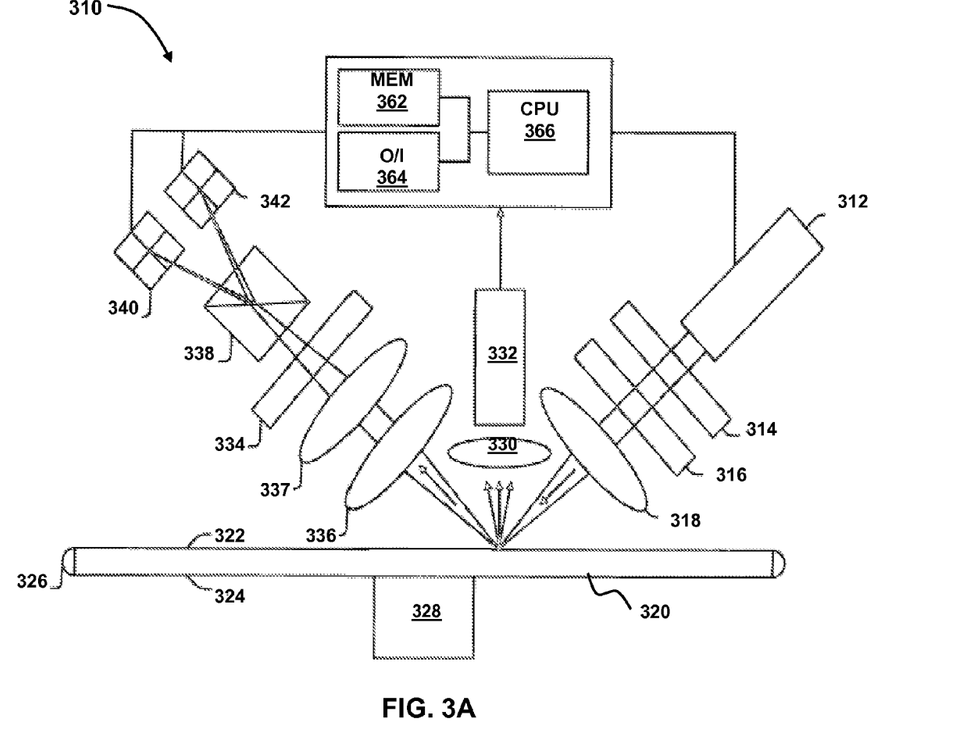
FIGS. 3A-3C are schematic diagrams illustrating a substrate edge inspection tool.
Figure 3B:
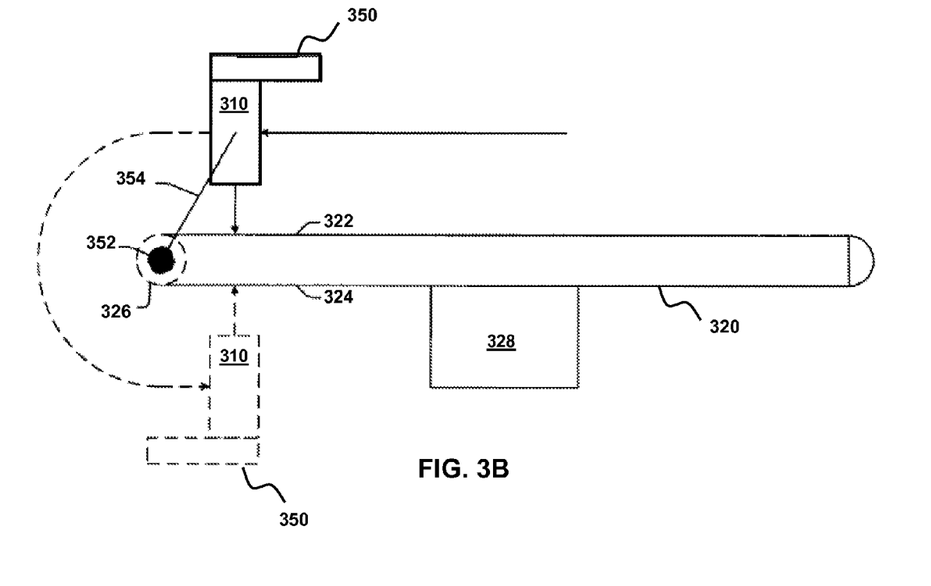

FIGS. 3A-3B area schematic diagrams illustrating a substrate edge inspection tools that may be used in systems of the types as described in FIGS. 1A-1B and FIG. 2. As shown in FIG. 3A, a surface analyzer assembly 310 may be positioned to direct radiation onto a surface of substrate 320. The substrate 320 may include an upper surface 322, a lower surface 324 and an edge surface 326. Surface analyzer assembly 310 may include a laser diode 312, an optical polarizer 314, an optional half-wave plate 316 and a focusing lens 318 for directing radiation onto the surface of the substrate 320. Surface analyzer assembly 310 also includes a collecting lens 330, a photomultiplier tube (PMT) 332, a collimating lens 336, a wobble reduction lens 337, a quarter wave plate 334, a Wollaston prism 338 rotated at 45 degrees to the plane of incidence, and two quadrant detectors 340, 342. Surface analyzer assembly 310 may include a central processor unit (CPU) 366 and a memory 362 (e.g., RAM, DRAM, ROM, and the like) and output/input (O/I) circuits 364.

As shown in FIG. 3B, the substrate 320 may be rotated about a central axis on a spindle 328 during an inspection process, which may be connected to a suitable motor or other drive assembly for inducing rotational motion to the spindle. A first drive assembly including, e.g., a motor 350 for moving the head in the horizontal direction. A second drive assembly including, e.g., a rotational motor 352 connected to the surface analyzer assembly 310 by a suitable linkage 354 provides rotational motion to move the surface analyzer assembly 310 around the edge surface 326 of the substrate 320. Such a system is described, e.g., in U.S. Pat. No. 7,161,668, the disclosures of which are incorporated herein by reference.

Figure 3C:
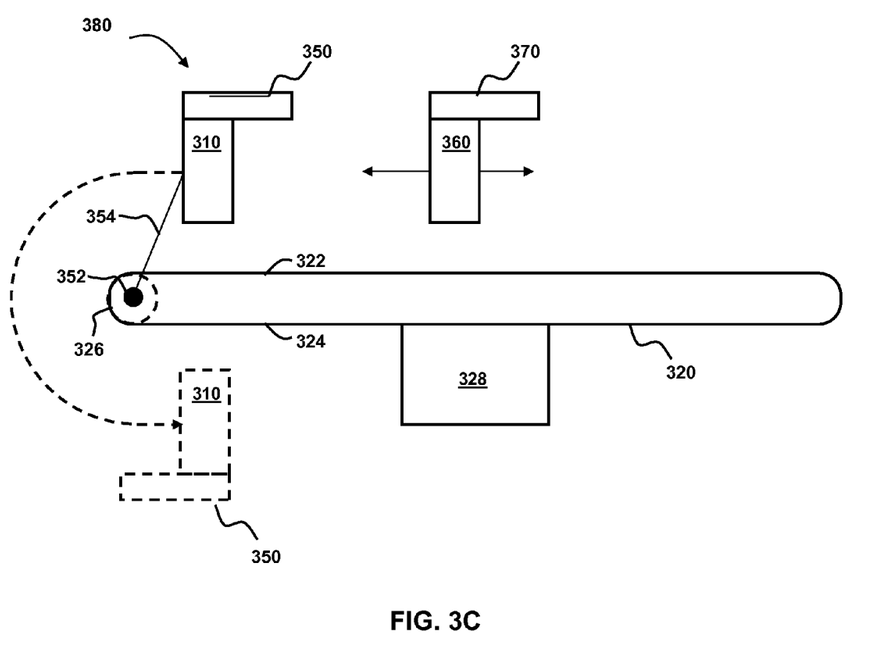

As shown in FIG. 3C, an edge inspection tool of the type shown in FIG. 3B may be integrated on a main stage of a surface inspection tool to produce a combined surface and edge inspection system 380. Specifically, the system 380 would include a first surface analyzer assembly 310 configured for edge inspection tool as described above, and a second surface analyzer assembly 360 configured for surface inspection. The second surface analyzer assembly 360 may be coupled to a second drive assembly 370 for moving the assembly in a horizontal direction relative to the substrate 320. This may involve modification of an existing surface inspection tool stage to allow for spinning of the substrate.

Figure 4:
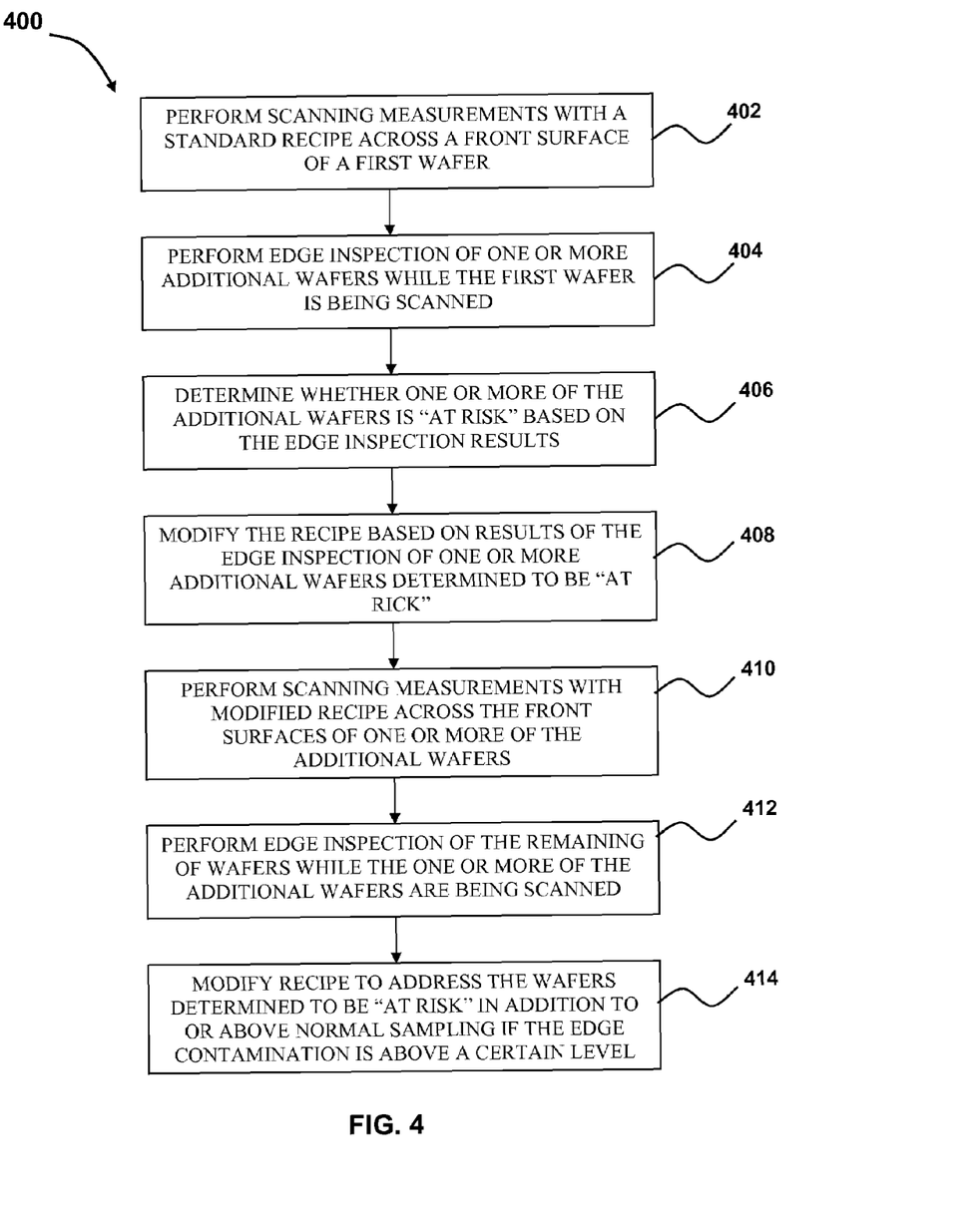
FIG. 4 is a flow diagram illustrating a method for inspecting substrates according to an embodiment of the present invention.

FIG. 4 is a flow diagram illustrating a method 400 for inspecting substrates that uses a combination of front surface inspection and edge inspection. As indicated in 402, when a substrate pod arrives on a surface inspection tool, preferably a bright field inspection tool, the first substrate is scanned across a front surface with a standard bright field recipe. While the first substrate is being scanned, edge inspection of one or more additional substrates may be performed as indicated in 404. By way of example, for a 20-substrate batch, edge inspection may be done for up to 50% or more of the batch while the first substrate is being scanned. As indicated at 406 a determination may be made as to whether one or more of the additional substrates is "at risk" based on a result of the edge inspection. In addition, the nature and/or pattern of edge defects in the edge inspection results may be used to determine a region of the substrate surface that is at-risk for defects. Determining whether a substrate is "at risk" may optionally include determining one or more "at risk" surface regions on the substrate that are more likely to be the location of surface defects based on the types of edge defects that are found and on whether the defects are concentrated in some particular portion of the edge. For example a substrate may be determined to be "at-risk" if it is found to have greater than a threshold number of edge defects or having one or more defects above a certain threshold size. Alternatively, an "expanded" or "cone shadow area" on a given substrate may be found to be at risk, based on the edge inspection results, such as the threshold vs. percent of length of perimeters impacted, defect types, defect sizes.

Figure 5A:
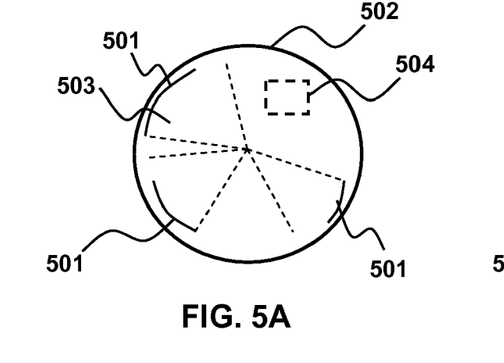
FIGS. 5A-5C are top views illustrating edge defect patterns correlated to process steps taking place before the substrate inspection step.
Figure 5B:
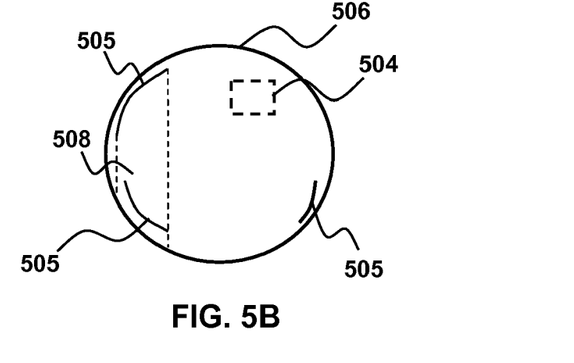
Figure 5C:
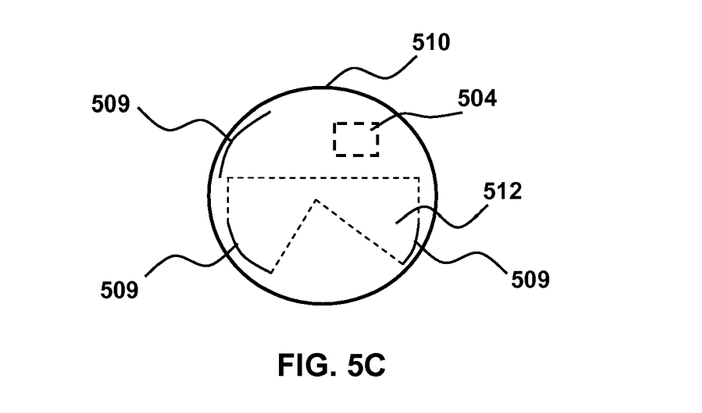

In 408, the bright field recipe may be automatically modified to allow scanning of the one or more of the additional substrates that are determined to be "at risk" based on results of the edge inspection. The bright field recipe may be modified to allow scanning of the "at risk" surface regions of the additional substrates. Edge defect patterns may be correlated to one or more processes to which the substrates are subjected prior to inspection. Modification of the bright field recipe may therefore depend on one or more process steps taking prior to the inspection process. For example, FIGS. 5A-5C illustrates three edge defect patterns for substrates that have undergone three different process steps. Knowledge of the edge defect pattern associated with the process step may be used to identify one or more at-risk regions on the surfaces of the substrates. It is noted that similar-looking edge defect patterns may lead to different assumptions about the at-risk region based on the nature of the process that the substrate has undergone. For example, FIG. 5A shows a pattern of edge defects 501 on a substrate 502 after a circular pattern process such as a Chemical Mechanical Planarization (CMP) process, which includes pressing a polishing "head" on the rotating substrate against a flexible pad. The rotationally symmetric nature of CMP combined with the observed pattern of defects 501 suggests one or more wedge-shaped at-risk regions 503. It is noted that this at-risk region is different from a potential reference area 504 that might otherwise be defined for the bright field recipe. The recipe may be modified to initially probe the at-risk region 503. This improves the chance that the modified recipe will locate defects more quickly than the unmodified recipe.

FIG. 5B shows a pattern of edge defects 505 of a substrate 506 after a wet cleaning process. Note that this pattern is very similar to the pattern shown in FIG. 5A. However, since a wet cleaning process may involve vertical extraction of the substrate 506 after immersion in a wet bath, defects might tend to concentrate at one end of the substrate 506. Consequently, the pattern of edge defects 505 and the known process tend to suggest an at-risk region 508 concentrated at one end of the substrate 506. Again, the bright field recipe may be modified to probe at-risk region 508 instead of the reference area 504.

FIG. 5C shows a pattern of edge defects 509 for a substrate 510 after a growth process, such as a "bottom-up" plating of the sub-micron scale features on the substrate surface, with a gas flow injector located at the bottom of the oven. Again, the pattern of the defects 509 is very similar to that shown in FIGS. 5A-5B. However, in this case, the combination of the known process and the pattern of the defects suggest an at-risk area 512 having two more or less wedge-shaped lobes.

Specifically, a known location of the gas injector in the oven and flow pattern of gas may suggest the shape of the at-risk area 512.

As indicated in 410, one or more of the additional substrates may be scanned with the modified recipe across the areas of interest (e.g., at-risk areas 503,508, 512). The remaining substrates may be edge inspected while the one or more of the additional substrates are scanned as indicated in 412. If an edge contamination is above a certain level, the recipe may be modified to address the substrates determined to be "at risk" in addition to or above a normal sampling as indicated in 414.

Figure 6:
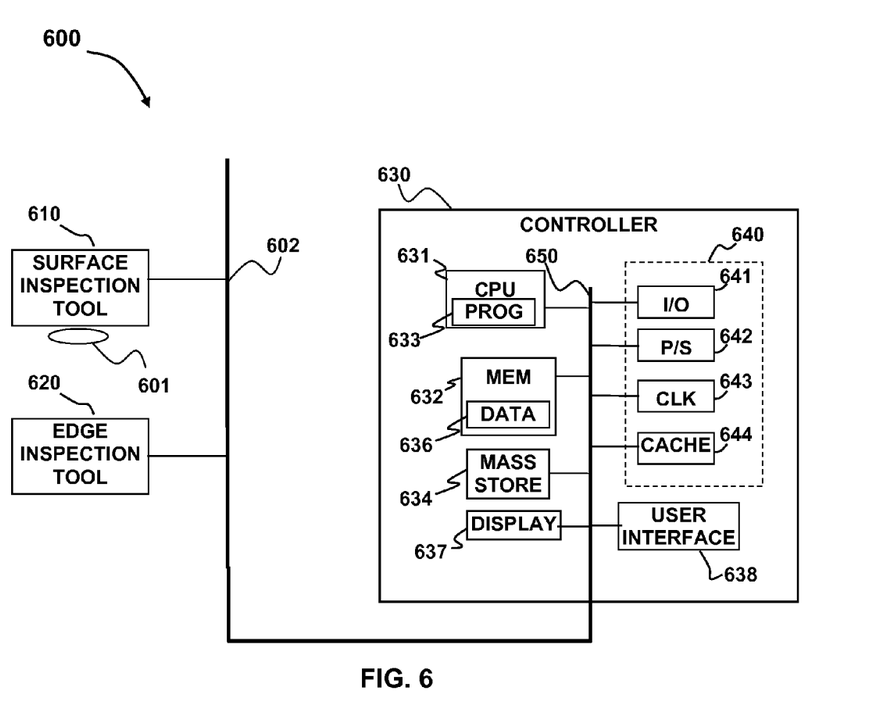
FIG. 6 is a block diagram illustrating an apparatus according to an embodiment of the present invention.

FIG. 6 illustrates an apparatus 600 that according to an embodiment of the present invention. The apparatus 600 includes a surface inspection tool 610, an edge inspection tool 620 and a controller 630. The surface inspection tool 610 and the edge inspection tool 620 are of the type of the surface inspection tool 104 and the edge inspection tool 102 as described in FIGS. 1A-1B, which can be bright or dark field inspection tools.

The inspection tools 610, 620 and controller 630 may communicate with each other through a data bus 602. The controller 630 may include a central processor unit (CPU) 631 and a memory 632 (e.g., RAM, DRAM, ROM, and the like). The CPU 631 may execute a process-control program 633, portions of which may be stored in the memory 632. The process control program 633 may include instructions for implementing a method for inspecting substrates as described in FIG. 4. The memory may contain data 636 related to surface inspections performed on one or more substrates by the surface inspection tool 610 and/or data related to edge inspections performed on one or more substrates 601 by the edge inspection tool 620. The controller 630 may also include well-known support circuits 640, such as input/output (I/O) circuits 641, power supplies (P/S) 642, a clock (CLK) 643 and cache 644. The controller 630 may optionally include a mass storage device 634 such as a disk drive, CD-ROM drive, tape drive, or the like to store programs and/or data. The controller 630 may also optionally include a display unit 637 and user interface unit 638 to facilitate interaction between the controller 630 and a user. The display unit 637 may be in the form of a cathode ray tube (CRT) or flat panel screen that displays text, numerals, or graphical symbols. The user interface 638 may include a keyboard, mouse, joystick, light pen or other device. The preceding components may exchange signals with each other via an internal system bus 650. The controller 630 may be a general purpose computer that becomes a special purpose computer when running code that implements embodiments of the present invention as described herein.

The surface and edge inspection systems as described in FIGS. 1A-1B and FIG. 2 and the method for inspecting substrates as described in FIG. 4 may allow for a decrease in sampling, e.g., to about 2-3 substrates per 20-substrate batch. Such a decrease in sampling may increase the substrate throughput and reduce the cost of ownership in a semiconductor manufacturing facility. Although the examples described above may relate to surface and edge inspection on semiconductor wafers, those of skill in the art will recognize that embodiments of the invention may be applied to surface and edge inspection of other substrates, such as reticles, flat panels, MEMS, optical lens and other manufacturing requiring the combination of front face and edge control.

While the above is a complete description of the preferred embodiment of the present invention, it is possible to use various alternatives, modifications and equivalents. Therefore, the scope of the present invention should be determined not with reference to the above description but should, instead, be determined with reference to the appended claims, along with their full scope of equivalents. Any feature, whether preferred or not, may be combined with any other feature, whether preferred or not. In the claims that follow, the indefinite article "A", or "An" refers to a quantity of one or more of the item following the article, except where expressly stated otherwise. The appended claims are not to be interpreted as including means-plus-function limitations, unless such a limitation is explicitly recited in a given claim using the phrase "means for."

What is claimed is:

1. A method for inspecting substrates, comprising:
   a) performing a scanning measurement across a front surface of a first substrate with a surface inspection tool according to a standard recipe;
   b) performing an edge inspection of one or more additional substrates with an edge inspection tool before or while performing the scanning measurement;
   c) determining whether one or more of the additional substrates is "at risk" based on a result of the edge inspection;
   d) modifying the standard recipe based on the result of the edge inspection of one or more of the additional substrates determined to be "at risk", thereby producing a modified recipe; and
   e) performing a scanning measurement across a front surface of one or more of the additional substrates with the surface inspection tool according to the modified recipe.

2. The method of claim 1 further comprising:
   f) performing edge inspection of a remainder of the additional substrates with the edge inspection tool while performing a scanning measurement across a front surface of one or more of the additional substrates with the surface inspection tool according to the standard recipe; and
   g) modifying the standard recipe to address the substrates determined to be "at risk" in addition to or above a normal sampling if an edge contamination is above a certain level.

3. The method of claim 1 wherein performing the edge inspection includes performing edge inspection of two or more substrates with the edge inspection tool while performing a scanning measurement with the surface inspection tool according to a standard recipe across a front surface of another substrate.

4. The method of claim 1 wherein d) depends on one or more process steps taking place before a) and b).

5. The method of claim 1 wherein d) comprises identifying an area of interest on the front surface of the substrates for the scanning measurement in e).

6. The method of claim 5 wherein the area of interest depends on an edge defect pattern for one or more of the additional substrates.

7. The method of claim 6 wherein d) comprises correlating the edge defect pattern to the one or more process steps taking place before a) and b).

8. The method of claim 1 wherein the one or more additional substrates include two or more additional substrates.

9. The method of claim 1 wherein the first substrate and the one or more additional substrates are semiconductor wafers.

10. The method of claim 1 wherein the first substrate and the one or more additional substrates are reticles, flat panels, MEMS or optical lenses.

11. A processor readable medium having processor readable instructions embodied therein for implementing a method for inspecting substrates on an apparatus having a surface inspection tool and an edge inspection tool, the processor readable instructions comprising:
  an instruction for performing a scanning measurement across a front surface of a first substrate with the surface inspection tool according to a standard recipe;
  an instruction for performing edge inspection of one or more additional substrates while performing the scanning measurement;
  an instruction for determining whether one or more of the additional substrates is "at risk" based on a result of the edge inspection;
  an instruction for modifying the standard recipe based on the result of the edge inspection of one or more of the additional substrates determined to be "at risk", thereby producing a modified recipe; and
  an instruction for performing scanning measurement across front surfaces of one or more of the additional substrates with the surface inspection tool according to the modified recipe.

* * * * *